United States Patent
Sakata et al.

(10) Patent No.: US 6,645,750 B1
(45) Date of Patent: Nov. 11, 2003

(54) POLYNUCLEOTIDES ENCODING POLYPEPTIDES HAVING β-PRIMEVEROSIDASE ACTIVITY

(75) Inventors: Kanzo Sakata, Kyoto (JP); Masaharu Mizutani, Kyoto (JP)

(73) Assignee: Amano Enzyme Inc., Aichi (JP)

( * ) Notice: Subject to any disclaimer, the term of this patent is extended or adjusted under 35 U.S.C. 154(b) by 0 days.

(21) Appl. No.: 09/914,841

(22) PCT Filed: Mar. 2, 2000

(86) PCT No.: PCT/JP00/01242

§ 371 (c)(1),
(2), (4) Date: Sep. 4, 2001

(87) PCT Pub. No.: WO00/52177

PCT Pub. Date: Sep. 8, 2000

(30) Foreign Application Priority Data

Mar. 4, 1999 (JP) ............................................... 11-56299

(51) Int. Cl.[7] .......................... C12N 9/24; C12N 15/70; C12N 1/20; C12Q 1/34; C12P 21/06
(52) U.S. Cl. ........................ 435/200; 435/18; 435/69.1; 435/320.1; 435/325; 435/252.3; 435/252.33; 435/254.2; 536/23.2
(58) Field of Search ...................... 536/23.2; 435/320.1, 435/18, 69.1, 200, 325, 252.3, 252.33, 254.2

(56) References Cited

U.S. PATENT DOCUMENTS 5,352,607 A * 10/1994 Laine et al. ............ 435/252.33
5,693,519 A * 12/1997 Laine et al. ................ 435/209

FOREIGN PATENT DOCUMENTS

JP 8-140675 6/1996

OTHER PUBLICATIONS

Sambrook et al. Molecular Cloning, A Laboratory Manual 3rd Ed., pp. 6.53–6.58, Cold Spring Harbor Laboratory Press, Cold Spring Harbor, NY, 2001.*

The American Heritage Dictionary, 4th Ed., Houghton Mlfflin Company, 2000.*

Wang, J. et al. "Floral scent production in Clarkia breweri (Onagraceae)" Plant Physiology (1997) vol. 114, No. 1, p. 213–221.

Ichigo, H. et al. Summary of the studies on the scent evolution during flower opening Fragrance Journal (Feb. 1999) vol. 27, No. 2, p. 21–27.

Guo et al, *Biosci. Biotech. Biochemistry, Japan Soc. for Bioscience, Biotechnolgoy and Agrochem., Tokyo Japan,* 11(60): 1810–1814 (1996).

EMBL Database Accession No. U26025, XP002205482, May 31, 1995.

Ijima et al, *J. of Agricultural and Food Chem., American Chem. Soc., Washington, US,* 46(5):1712–1718 (1998).

Ogawa et al, *J. of Agricultural and Food Chem.,* 45(3):877–882 (1997).

Guo et al, *Biosci. Biotech. Biochemistry, Japan Soc. for Bioscience, Biotechnology and Agrochem., Tokyo Japan,* 5(59):962–964 (1995).

* cited by examiner

*Primary Examiner*—Rebecca E. Prouty
*Assistant Examiner*—Delia Ramirez
(74) *Attorney, Agent, or Firm*—Sughrue Mion, PLLC

(57) ABSTRACT

A β-primeverosidase gene characterized by encoding a protein containing the amino acid sequence represented by SEQ ID NO:1 in the Sequence Listing or an amino acid sequence derived from this sequence by deletion, substitution, insertion or addition of one or more amino acids and utilization thereof.

9 Claims, No Drawings

US 6,645,750 B1

POLYNUCLEOTIDES ENCODING POLYPEPTIDES HAVING β-PRIMEVEROSIDASE ACTIVITY

TECHNICAL FIELD

This invention relates to a β-primeverosidase of a plant. β-Primeverosidase is an enzyme acting on β-primeveroside, which is a disaccharide glycoside, and catalyzing a reaction of forming aroma components of tea and primeverose.

BACKGROUND ART

In the studies on aroma components of plants, there has been confirmed the presence of a disaccharide glycoside β-primeveroside (6-O-β-D-xylopyranosyl-β-D-glucopyranoside) and its analogs, as precursors for alcoholic aroma components such as geraniol and linalol. Also, it has been clarified that β-primeveroside, a disaccharide glycoside, and its analogs exist as precursors for alcoholic aroma components other than those cited above.

The invention relates to a β-primeverosidase gene of a plant. β-Primeverosidase is an enzyme acting on β-primeveroside, which is a disaccharide glycoside, and catalyzing a reaction of forming aroma components of tea and primeverose.

The term "β-primeverosidase" means an enzyme having an enzymatic activity of cleaving disaccharide glycosides (in particular, β-primeveroside and its analogs) in a disaccharide unit. The enzyme according to the invention is characterized by having an activity of acting on a disaccharide glycoside, which is hardly usable as a substrate by the existing glucosidase, and thus releasing saccharides in a disaccharide unit from this disaccharide glycoside. An enzyme having the above activity is called "β-primeverosidase" herein.

Concerning the presence of an enzyme specifically acting on these disaccharides, the inventors first studied β-primeverosidase which is an enzyme forming the aroma components of tea. Thus, they isolated this enzyme and clarified its properties (JP-A-8-140675; the term "JP-A" as used herein means an "unexamined published Japanese patent application").

However, the nucleotide sequence, etc. of this enzyme have not been clarified hitherto and no study has been made on the isolation and utilization of its gene.

DISCLOSURE OF THE INVENTION

An object of the invention is to provide means for isolating β-primeverosidase gene originating in a plant, in particular tea, and thus providing this enzyme at a lower cost. The invention makes it possible to broaden the application range of the β-primeverosidase originating in a plant.

To achieve the above-described object, the inventors have conducted intensive studies and, as a result, completed the invention.

Namely, the gist of the invention resides in a DNA which encodes a protein comprising the amino acid sequence represented by SEQ ID NO:1 in Sequence Listing or an amino acid sequence derived from this sequence by deletion, substitution, insertion or addition of one or more amino acids.

Particular examples of the above-described DNA include the following DNAs. Namely, DNA having the nucleotide sequence represented by SEQ ID NO:2 in Sequence Listing, or a DNA as described in claim 1 which encodes a protein comprising a polynucleotide selected from the following polynucleotides (a) to (g) and has a primeverosidase activity:

(a) a polynucleotide encoding a polypeptide having the amino acid sequence represented by SEQ ID NO:1 in Sequence Listing;
(b) a polynucleotide encoding a polypeptide having an amino acid sequence derived from the amino acid sequence represented by SEQ ID NO:1 in Sequence Listing by deletion, addition, insertion or substitution of one or more amino acid residues;
(c) a polynucleotide having the nucleotide sequence represented by SEQ ID NO:2 in Sequence Listing;
(d) a polynucleotide having a nucleotide sequence derived from the nucleotide sequence represented by SEQ ID NO:2 in Sequence Listing by deletion, addition, insertion or substitution of one or more bases;
(e) a gene capable of hybridizing with one of the polynucleotides (a) to (d) as described above under stringent conditions;
(f) a polynucleotide having a homology with one of the polynucleotides (a) to (d) as described above; and
(g) a polynucleotide which is degenerate with respect to at least one of the polynucleotides (a) to (f) as described above.

Now, the invention will be described in detail. The DNA according to the invention is a DNA encoding the above-described protein. To complete the invention, this DNA could be isolated from a tea cDNA library as will be described hereinafter. However, its nucleotide sequence has been clarified by the invention and, therefore, it can be obtained by chemical synthesis on the basis of the sequence represented by SEQ ID NO:1 or 2.

Alternatively, the DNA according to the invention can be obtained from a tea chromosomal DNA library or DNA libraries of other plants by the PCR or hybridization method known per se with the use of synthetic oligonucleotide probes or oligonucleotide primers synthesized on the basis of these sequences.

Next, illustration will be made by reference to examples of a method of obtaining the DNA according to the invention by acquiring a part of the DNA of the invention from a tea cDNA library by PCR followed by hybridization by using it as a probe, and a method of producing β-primeverosidase from *Escherichia coli* or a yeast by a gene recombination method with the use of the thus obtained DNA.

It is widely recognized by those skilled in the art in general that an amino acid sequence encoding a physiologically active protein sometimes sustains its physiological activity in case of having deletion, substitution, insertion or addition of one or more amino acids. As a matter of course, the invention involves in the scope thereof DNA fragments having these modifications and yet encoding proteins having the β-primeverosidase activity.

That is to say, the invention involves in the scope thereof DNAs encoding proteins which comprise amino acid sequences derived from the sequence represented by SEQ ID NO:1 in Sequence Listing by deletion, substitution, insertion or addition of one or more amino acids and have the β-primeverosidase activity. Such a modified DNA can be obtained by modifying the nucleotide sequence of the invention so as to delete, substitute, insert or add amino acid(s) at specific site(s) by, for example, the site-directed mutagenesis method.

Alternatively, a modified DNA can be obtained by mutagenesis of the DNA according to the invention or cells having the same and selecting a DNA which is hybridizable with the DNA having, for example, the nucleotide sequence represented by SEQ ID NO:2 in Sequence Listing under stringent conditions from the DNAs or cells obtained above.

The term "stringent conditions" as used herein means such conditions that allow the formation of so-called specific hybrids but not unspecific hybrids. Although these conditions can be hardly defined numerically, citation may be made of conditions under which nucleic acids having a high homology with each other (for example, DNAs having a 70 to 90% or more homology with each other) are hybridized but nucleic acids having a lower homology with each other cannot be hybridized.

The "stringent conditions" may be exemplified by 6×SSC, 1.0% of a blocking agent, 0.1% of N-lauroylsarcocine sodium and 0.02% of SDS.

It is also possible to obtain a β-primeverosidase gene from tea chromosome by a conventional method with the use of the DNA according to the invention or a part thereof as a probe. However, it is expected that the β-primeverosidase gene originating in tea chromosome contains intron(s). Such a DNA having an intervening intron also falls within the scope of the DNA according to the invention, so long as it encodes the β-primeverosidase of the invention.

Moreover, the invention involves in its scope a protein which comprises an amino acid sequence derived from the amino acid sequence represented by SEQ ID NO:1 in Sequence Listing by deletion, substitution, insertion or addition of one or more amino acids but has no β-primeverosidase activity, so long as a protein having the β-primeverosidase activity can be obtained therefrom by a simple treatment such as splicing or treating with a protease. Examples of such case include a protein having the amino acid sequence represented by SEQ ID NO:15 and proteins having amino acid sequences derived from the amino acid sequence represented by SEQ ID NO:15 by deletion, substitution, insertion or addition of one or more arbitrary amino acids in the region from the N-terminal −78 to −1 positions.

Furthermore, the invention involves in its scope fused proteins composed of a protein having an amino acid sequence derived from the amino acid sequence represented by SEQ ID NO:1 by deletion, substitution, insertion or addition of one or more amino acids with another protein. Examples thereof include proteins employed in fused protein expression systems (for example, maltose-binding protein: Pascale Duplay et al., Journal Biological Chemistry, Vol. 259, pp. 10606–10613 (1984)).

Further, a transformant capable of producing β-primeverosidase can be selected by integrating the obtained β-primeverosidase gene into an appropriate vector, transforming *E. coli*, yeasts, cultured cells, plants, etc. therewith, and then screening.

When cultured in a nutrient medium, the transformant thus obtained stably produces a peptide having a high β-primeverosidase activity. The culture conditions in culturing the transformant may be appropriately selected by taking the nutritional and physiological properties of the host into consideration. Although liquid culture is usually carried out in many cases, submerged aeration-agitation culture is industrially advantageous. As a carbon source, any carbon compound may be used so long as it is metabolizable. For example, use can be made of glucose, lactose, maltose and the like. As a nitrogen source, any nitrogen compound may be used so long as it is usable. For example, use can be made of yeast extract, peptone, meat extract and the like. The culture temperature is controlled to such a level as allowing the production of β-primeverosidase. In case of *E.coli* or yeasts, the culture temperature usually ranges from 10 to 42° C. To express the β-primeverosidase according to the invention in *E.coli* or yeasts, it is preferable to use a culture temperature of 20° C. or lower, still preferably from about 10 to about 20° C.

The culture may be carried out for a period of time of attaining the maximum yield of β-primeverosidase. The culture is usually continued for 12 to 72 hours. The pH value of the medium may be controlled so as to allow the growth of the cells and stably produce β-primeverosidase, preferably from pH 6 to 8.

Though the presence of the β-primeverosidase gene originating in tea according to the invention had been clarified, it was highly difficult to confirm its activity. In the invention, it has been clarified that the expression of a mature protein as an active protein can be achieved by carrying out culturing under specific conditions by using a fused protein expression system.

That is to say, the expression could be first achieved by carrying out the culturing at 20° C. or lower to thereby slow down the protein production speed compared with usual cases. In particular, expression in *E.coli* can be established by forming an inducible fused protein and thus slowing down the protein production. As the fused protein, it is favorable to use a protein fused with maltose-binding protein. It is also favorable that the production at a low speed is carried out by using promoters which can be artificially controlled (promoters lac, tac, etc.) and an inducer (for example, IPTG) at a lower concentration (1 mM or lower, preferably about 0.1 mM) than that in usual cases.

The β-primeverosidase thus produced may be subjected to various treatments depending on the purpose. In case where the β-primeverosidase is contained in cells, the cells are harvested by filtration, centrifugation, etc. and then disrupted by a physical method with the use of a machine or an enzymatic method with the use of lysozyme, etc. followed by extraction. Moreover, the β-primeverosidase thus obtained may be salted out, concentrated, purified, etc., if needed.

Unless otherwise noted, the β-primeverosidase activity described herein was measured in the following manner.

(1) β-Primeverosidase Activity

The enzyme activity was examined by using p-nitrophenyl-β-primeveroside (pNP-Pri) as a substrate and measuring p-nitrophenol (pNP) released therefrom with a spectrophotometer. The unit of enzyme activity was defined as the release of 1 μmol of pNP per minute.

More particularly, 300 μl of a sample to be assayed, 1100 μl of a 20 mM citrate buffer solution (pH 6.0) and 300 μl of a 10 mM solution of pNP-Pri in the same buffer solution were mixed and incubated at 37° C. After 30, 60, 90 and 120 minutes, the liquid reaction mixture was sampled in 340 μl portions and the reaction was stopped by adding 170 μl of a 1 M aqueous solution of sodium carbonate. Then the absorbance at 405 nm was measured with a spectrophotometer.

The pNP-primeveroside serving as the substrate can be synthesized by, for example, reacting pNP-glucoside (manufactured by Merck & Co., Inc.) with xylooligosaccharide (manufactured by Wako Pure Chemical Industries, Ltd.) by using an enzyme xylosidase (manufactured by Sigma Chemical Co.) and thus transferring one xylose residue to the pNP-glycoside via a β-1,6 bond.

(2) β-Glucosidase Activity

The enzyme activity was measured as in the measurement of the β-primeverosidase activity (1) by using p-nitrophenyl-β-glucoside as a substrate.

BEST MODE FOR CARRYING OUT THE INVENTION

Now, the invention will be described in greater detail by reference to the following Examples. Needless to say, the invention is not construed as being limited thereto without departing from the gist of the invention. Unless other wise noted, all percentages are expressed in w/v % in this specification.

EXAMPLE 1

Preparation of Crude Enzyme Solution

Fresh tea leaves (cultivar: Yabukita) were ground in acetone under cooling with dry ice. Then the residue was washed with acetone at −20° C. until the filtrate became almost colorless and dried to give an acetone powder.

This acetone powder was suspended in 1 l of a 0.1 M citrate buffer solution (pH 6.0) and stirred at 4° C. for 3 hours to thereby extract the enzyme. The extract was centrifuged and the residue was discarded. To the supernatant was added the equal amount of acetone and the resultant mixture was stirred and then allowed to stand at 4° C. overnight. Then the protein fraction was precipitated. Next, the precipitate was collected by centrifugation, dissolved in a citrate buffer solution and salted out against ammonium sulfate. The precipitate in the 40–80% ammonium sulfate-saturation fractions were dissolved in a 20 mM citrate buffer solution and then dialyzed against the same buffer solution.

EXAMPLE 2

Purification of β-Primeverosidase

The enzyme activity was examined by using p-nitrophenyl-β-primeveroside (pNP-Pri) as a substrate and measuring p-nitrophenol (pNP) released therefrom with a spectrophotometer. The unit of enzyme activity was defined as the release of 1 μmol of pNP per minute.

After the completion of the dialysis, the enzyme fraction was passed through a CM-Toyopearl 650 column (manufactured by Tosoh Corporation) having been equilibrated with a 20 mM citrate buffer solution and the adsorbed fraction was eluted and collected by using the same buffer solution containing 0 to 0.5M of NaCl. The enzyme fraction thus collected was concentrated with an ultrafiltration membrane (Amicon PM-10, manufactured by Grace Japan K.K.) and Centricon 10 (manufactured by Grace Japan K.K.). Next, it was passed through Mono S HR (Pharmacia Biotech) having been equilibrated with a 20 mM citrate buffer solution and the enzyme fraction thus adsorbed was eluted and collected by using the same buffer solution containing 0 to 0.2 M of NaCl.

EXAMPLE 3

Determination of the Amino Acid Sequence of Tea Primeverosidase

The purified primeverosidase was partially digested by trypsin and subjected to separation and purification by reversed phase chromatography to give a peptide fragment. The amino acid sequence of the peptide fragment thus obtained was determined with an amino acid sequencer. Thus the following amino acid sequence was obtained.
[SEQ ID NO:3]
wherein Xaa stands for an unknown amino acid.

EXAMPLE 4

Isolation of Tea Primeverosidase Gene Clone

Total RNA was extracted from Yabukita tea leaves by using an RNA extraction kit (Pharmacia Biotech). Poly(A)+ RNA was prepared by using an oligo dT column and a cDNA library was constructed by using a λ vector in accordance with the instruction of λZAPII-cDNA Synthesis Kit (manufactured by Stratagene). This λ vector was excised into a phagemid by in vitro excision to thereby give a cDNA library of plasmid type.

Next, PCR was performed by using as PCR primers an oligonucleotide probe B GLU1 synthesized on the basis of the amino acid sequence of this peptide fragment:
[SEQ ID NO:4]
and a −20 primer on pBluescriptSK+vector:
[SEQ ID NO:5]
and the cDNA library of plasmid type as prepared above as a template, thereby giving a DNA fragment. By using this fragment as a probe, positive clones were obtained from the Yabukita cultivar λZAPII-cDNA library with the use of a DIG System (Boehringer-Mannheim). Among 15 positive clones, the one having the longest DNA insert was selected and a phagemid pBluescriptSK+ was prepared by in vivo excion to thereby determine the nucleotide sequence of the DNA insert. As a result, it was clarified that a gene fragment (SEQ ID NO:14) containing an open reading frame (ORF) consisting of the full length 507 amino acids (SEQ ID NO:15) including the thus determined amino acid sequence was obtained. SEQ ID NO:1 shows the mature protein part while SEQ ID NO:2 shows the nucleotide sequence corresponding thereto.

EXAMPLE 5

(1) Expression of Tea Primeverosidase Gene (1)

To confirm whether or not the gene thus cloned was a primeverosidase gene, an attempt was made to express the obtained cDNA. Since there had been reported the expression of the activities of several enzyme genes originating in plants in *E.coli*, it was attempted to express the gene in *E.coli*. By using the gene fragment containing the part encoding 507 amino acid residues as a template, amplification was carried out by the PCR method with the use of primers NN1:
[SEQ ID NO:6]
and MM2:
[SEQ ID NO:7]
to give a fragment. The fragment thus obtained had BamHI site and SalI site respectively introduced into the upstream and downstream of ORF. The fragment was cut out by restriction enzymes BamHI and SalI and inserted into the BamHI and SalI sites of an expression vector pKK233-3 (Pharmacia Biotech), thereby giving pKK233-3Pri. Subsequently, *E.coli*. JM105 was transformed with pKK233-3Pri. The transformed *E.coli* was inoculated into 100 ml of LB medium and cultured at 37° C. for 135 minutes. After adding IPTG at a final concentration of 0.1 mM, the culture was continued for additional 21 hours. After the completion of the culture, cells were collected by centrifugation, re-suspended in 4 ml of a column buffer solution (20 mM Tris HCl, 200 mM NaCl, 1 mM EDTA, 10 mM 2-mercaptoethanol, pH 7.4) and ultrasonically disrupted with a Branson Sonifier 250. After centrifuging, the supernatant and the precipitate were referred to respectively as a soluble fraction and an insoluble fraction.

To measure the primeverosidase activity, 300 μl of the soluble fraction was mixed with 1100 μl of a 20 mM citrate buffer solution (pH 6.0) and 300 μl of a 10 mM solution of pNP-Pri in the same buffer solution and incubated at 37° C. After 30, 60, 90 and 120 minutes, the liquid reaction mixture was sampled in 340 μl portions and the reaction was stopped by adding 170 µl of a 1 M aqueous solution of sodium carbonate. Then the release of pNP was monitored by measuring the absorbance at 405 nm with a spectrophotometer. As a result, no enzyme activity was observed.

(2) Expression of Tea Primeverosidase Gene (2)

A comparison of the amino acid sequence of the obtained cDNA clone with the terminal amino acid sequence determined from the protein indicated that the tea primeverosidase might be in the precursor structure. By analyzing the amino acid composition deduced on the basis of the open reading frame of the obtained cDNA, it was assumed that the region from the initiation codon to the amino acid at the 28-position would be a signal sequence-like region being rich in hydrophobic amino acids. From the viewpoint that the expression would be inhibited by this part, a gene fragment from which this part had been deleted was constructed. Namely, the maturation part was amplified as a fragment by the PCR method with the use of a primer MM1:
[SEQ ID NO:8]
and the above-described primer MM2:
[SEQ ID NO:9]
and the cloned gene as a template. The amplified fragment was cleaved with BamHI and SalI and inserted into the BamHI and SalI sites of a fused protein expression vectors pQE30 (manufactured by Quiagen), pRSETA (manufactured by Invitorgen) and pGEX4 (manufactured by Pharmacia Biotech). Then *E.coli* JM109 was transformed with the thus obtained vectors pQE30ΔPri, pRSETAΔPri and pGEX4ΔPri. The *E.coli* transformants were each inoculated into 100 ml of LB medium and cultured at 37° C. for 135 minutes. After adding IPTG at a final concentration of 0.1 mM, the culture was continued for additional 21 hours. After the completion of the culture, cells were collected by centrifugation and a soluble fraction was prepared by the method as described above. Then the primeverosidase activity was measured. As a result, no activity was detected in all of the cases.

(3) Expression of Tea Primeverosidase Gene (3)

It was assumed that the failure in the confirmation of the expression might be caused by the inadequate concentration of IPTG (isopropyl-1-thio-β-galactopyranoside) added to the liquid culture medium for inducing the expression. Thus, JM109 transformants transformed by the vectors pQE30ΔPri, pRSETΔPri and pGEX4ΔPri were cultured under the above-described conditions but adding IPTG to give a final concentration of 0.1, 1 or 9 mM. After collecting the cells, soluble fractions were prepared and the activity was examined. As a result, no activity was observed in the soluble fractions.

(4) Expression of Tea Primeverosidase Gene (4)

The results of the attempts (1) to (3) to express the gene indicated that primeverosidase could be hardly expressed by usual methods. It was assumed that the expression could be hardly achieved since the enzyme synthesized in the cells might be present in an inactive state in the insoluble fraction. In the expression vectors pQE30ΔPri, pRSETAΔPri and pGEX4ΔPri, the gene inserted thereinto is expressed respectively as fused proteins of 54 kDa, 54 kDa and 81 kDa. When the insoluble fractions were analyzed by SDS-PAGE, proteins of the sizes corresponding to these fused proteins were observed in the respective insoluble fractions under the induction with IPTG. Therefore, it was considered that the gene had been expressed but resulted in transfer to the insoluble fraction in an inactive state.

After fully considering the above results, we considered that the inactivation of the expressed gene product could be prevented by culturing *E.coli* after the induction with IPTG at a temperature of 25° C., i.e., lower than the usual temperature of 37° C. Thus, it was attempted to express the *E.coli* gene by lowering the culture temperature from the usual level after the induction with IPTG. JM109 transformants having been transformed by the vectors pQE30ΔPri, pRSETAΔPri and pGEX4ΔPri were each inoculated into 100 ml of LB medium and cultured. After adding IPTG at a final concentration of 0.1 mM, each strain was cultured at 25 and 22° C. overnight or at 18° C. for 13 hours. The cells were collected and a soluble fraction was prepared by the above-described method. Then the primeverosidase activity was measured. As a result, no activity was detected.

(5) Expression of Tea Primeverosidase Gene (5)

Separately, an attempt was made to express the gene by using another fusion protein expression vector pMALc (manufactured by New England, Biolabs). Similar to the above-described case, a maturation part was amplified by PCR and inserted into the BamHI and SalI sites of the pMALc vector, thereby constructing pMALcΔPri. Then *E.coli* JM109 was transformed. The *E.coli* transformant was inoculated into 100 ml of LB medium and cultured at 37° C. for 135 minutes. After adding IPTG at a final concentration of 0.1 mM, the culture was continued for additional 21 hours. After the completion of the culture, the cells were collected by centrifuging and a soluble fraction was prepared by the above-described method. Then the primeverosidase activity was measured. As a result, no activity was detected in all of the cases. Since a protein of a molecular weight of 94 kDa (i.e., the fused protein) was observed in the insoluble fraction, it was considered that the expressed protein migrated into the insoluble fraction in an inactive state seemingly due to the insufficient folding in this case too.

After adding IPTG to give a final concentration of 0.1 mM, the culture temperature was then lowered from the usual level to 22, 18 and 10° C. and the culture was carried out for 24 hours. As a result, it was confirmed that the fused protein was present in each of the soluble fractions and the activity was also detected. Although β-glucosidase activity was measured in these soluble fractions, no activity was detected.

(6) Expression of Tea Primeverosidase Gene (6)

It was further attempted to express the gene in a yeast. Using pYES2 (manufactured by Invitrogen) as the expression vector, a gene fragment encoding a precursor was first amplified as a fragment by the PCR with the use of a primer NN1:
[SEQ ID NO:10]
and another primer MM3:
[SEQ ID NO:11]
and then inserted into the BamHI and XhoI sites of pYES2, thereby constructing pYES2Pri. Then a yeast strain INVSc1 was transformed. The yeast thus transformed was cultured in YPG medium at 30° C. for 24 hours. Then the cells were collected and ultrasonically disrupted in the same manner as described above to give a soluble fraction. Although the activity was measured, no activity could be detected. Next, the maturation part was amplified as a fragment by the PCR with the use of a primer MM1:

[SEQ ID NO:12]
and another primer MM3:
[SEQ ID NO:13]
and then inserted into the BamHI and XhoI sites of pYES2, thereby constructing pYES2Pri. Then a yeast strain INVSc1 was transformed thereby. The yeast thus transformed was cultured in YPG medium at 20 and 10° C. (i.e., lower by 30° C. than the usual culture temperature) for 72 hours. Then the cells were collected and ultrasonically disrupted in the same manner as described above to give a soluble fraction. When the activity was measured, the activity was detected in the soluble fraction. No p-glucosidase activity was observed in this soluble fraction.

Based on the results as described above, it is considered that the tea-origin primeverosidase gene was hardly expressed not because the expression system of *E. coli* was inappropriate but because the activity of the gene per se could be hardly expressed.

INDUSTRIAL APPLICABILITY

As discussed above, it is very difficult to confirm the activity by the expression of the primeverosidase gene originating in tea. It is found out that an active protein can be detected by forming a fused protein of the mature protein with a limited conventional protein under conditions not usually employed in culturing.

As the results of intensive studies, we have found out for the first time specific conditions appropriate for the expression of tea-origin primeverosidase and, indicated after many difficulties that the primeverosidase gene expresses its primeverosidase activity under these conditions.

Consequently, the gene sequence and the amino acid sequence of tea primeverosidase have been clarified for the first time.

What is claimed is:

1. An isolated polynucleotide, wherein said polynucleotide encodes a polypeptide comprising amino acids 1 to 429 of SEQ ID NO:1.

2. The isolated polynucleotide as claimed in claim 1, wherein said polynucleotide comprises nucleotides 1 to 1287 of SEQ ID NO:2.

3. An isolated polynucleotide wherein said polynucleotide encodes a polypeptide having β-primeverosidase activity, said activity catalyzing release of a disaccharide and an aglycan from a disaccharide glycoside, and wherein said polynucleotide has at least 90% sequence homology over the entire length to SEQ ID NO:2.

4. The isolated polynucleotide as claimed in claim 1, 2 or 3, wherein said polynucleotide is isolated from a plant.

5. The isolated polynucleotide as claimed in claim 4, wherein said plant is a tea plant.

6. A cloning or expression vector comprising an isolated polynucleotide as claimed in claim 1, 2 or 3.

7. A host cell transformed with the vector as claimed in claim 6.

8. The host cell as claimed in claim 7, wherein said host cell is *Escherichia coli* or a yeast.

9. A process for producing a polypeptide having β-primeverosidase activity comprising, (a) culturing the host cell as claimed in claim 7 under conditions suitable for expression of a polypeptide having β-primeverosidase activity, and (b) recovering a polypeptide having β-primeverosidase activity so expressed.

* * * * *

SEQUENCE LISTING

<160> NUMBER OF SEQ ID NOS: 15

<210> SEQ ID NO 1
<211> LENGTH: 429
<212> TYPE: PRT
<213> ORGANISM: Camellia var. sinensis

<400> SEQUENCE: 1

```
Ile Ser Asn Gly Ser Thr Gly Asp Val Ala Asp Asp Phe Tyr His Arg
1               5                   10                  15

Tyr Lys Glu Asp Val Lys Val Leu Lys Phe Ile Gly Leu Asp Gly Phe
            20                  25                  30

Arg Met Ser Ile Ser Trp Ala Arg Val Leu Pro Arg Gly Lys Leu Ser
        35                  40                  45

Gly Gly Val Asn Lys Glu Gly Ile Ala Phe Tyr Asn Asn Val Ile Asn
    50                  55                  60

Asp Leu Leu Ser Lys Gly Ile Gln Pro Phe Ile Thr Ile Phe His Trp
65                  70                  75                  80

Asp Leu Pro Gln Ala Leu Glu Asp Glu Tyr Gly Gly Phe Leu Ser Pro
                85                  90                  95

His Ile Val Asn Asp Phe Arg Asp Phe Ala Glu Leu Cys Phe Lys Glu
            100                 105                 110

Phe Gly Asp Arg Val Lys His Trp Ile Thr Met Asn Glu Pro Trp Ser
        115                 120                 125

Tyr Ser Tyr Gly Gly Tyr Asp Ala Gly Leu Leu Ala Pro Gly Arg Cys
    130                 135                 140

Ser Ala Phe Met Ala Phe Cys Pro Lys Gly Asn Ser Gly Thr Glu Pro
145                 150                 155                 160

Tyr Ile Val Thr His Asn Leu Leu Leu Ser His Ala Ala Val Lys
                165                 170                 175

Leu Tyr Lys Glu Lys Tyr Gln Ala Tyr Gln Lys Gly Gln Ile Gly Ile
            180                 185                 190

Thr Leu Val Thr Tyr Trp Met Ile Pro Tyr Ser Asn Ser Lys Ala Asp
        195                 200                 205

Lys Asp Ala Ala Gln Arg Ala Leu Asp Phe Met Tyr Gly Trp Phe Ile
    210                 215                 220
```

-continued

```
Glu Pro Leu Ser Phe Gly Glu Tyr Pro Lys Ser Met Arg Arg Leu Val
225                 230                 235                 240

Gly Lys Arg Leu Pro Arg Phe Thr Lys Glu Gln Ala Met Leu Val Lys
                245                 250                 255

Gly Ser Phe Asp Phe Leu Gly Leu Asn Tyr Tyr Ile Ala Asn Tyr Val
            260                 265                 270

Leu Asn Val Pro Thr Ser Asn Ser Val Asn Leu Ser Tyr Thr Thr Asp
        275                 280                 285

Ser Leu Ser Asn Gln Thr Ala Phe Arg Asn Gly Val Ala Ile Gly Arg
    290                 295                 300

Pro Thr Gly Val Pro Ala Phe Phe Met Tyr Pro Lys Gly Leu Lys Asp
305                 310                 315                 320

Leu Leu Val Tyr Thr Lys Glu Lys Tyr Asn Asp Pro Val Ile Tyr Ile
                325                 330                 335

Thr Glu Asn Gly Met Gly Asp Asn Asn Asn Val Thr Thr Glu Glu Gly
            340                 345                 350

Ile Lys Asp Pro Gln Arg Val Tyr Phe Tyr Asn Gln His Leu Leu Ser
        355                 360                 365

Leu Lys Asn Ala Ile Ala Ala Gly Val Lys Val Lys Gly Tyr Phe Thr
    370                 375                 380

Trp Ala Phe Leu Asp Asn Phe Glu Trp Leu Ser Gly Tyr Thr Gln Arg
385                 390                 395                 400

Phe Gly Ile Val Tyr Val Asp Phe Lys Asp Gly Leu Lys Arg Tyr Pro
                405                 410                 415

Lys His Ser Ala Leu Trp Phe Lys Lys Phe Leu Leu Lys
                420                 425

<210> SEQ ID NO 2
<211> LENGTH: 1287
<212> TYPE: DNA
<213> ORGANISM: Camellia var. sinensis

<400> SEQUENCE: 2
atatcgaatg gtagcactgg agatgtagct gatgactttt atcatcgtta caaggaagat    60
gtgaaggtgc tgaagtttat aggactagat ggtttcagaa tgtccatctc atgggcccga   120
gtattacctc gggggaagct agcggagga gtgaacaagg aaggtatcgc cttctacaac   180
aatgtcatca atgaccttt atcgaaaggt atacaacctt ttataacaat ctttcactgg   240
gatcttcccc aagccctaga agatgaatat ggaggctttt taagcccaca cattgtgaac   300
gatttccggg atttttgcaga gctgtgcttc aaggagtttg gtgaccgagt taaacattgg   360
atcacaatga atgaaccatg gtcttactcc tatggggtt atgatgcagg tctcctagca   420
ccgggccgtt gttcggcttt tatggcattt tgccctaaag ggaattctgg gactgagccc   480
tatatagtta cccacaattt gcttctttct catgctgctg ctgtgaaact atacaaggag   540
aaatatcagg catatcaaaa ggggcagata gggataacac tagtgactta ttggatgatt   600
ccctactcca attcgaaagc cgacaaggat gcagcacaac gagcccttga tttcatgtat   660
ggatggttta ttgagccatt aagctttggt gaatatccaa aaagcatgcg tagactcgtt   720
ggtaaaaggt taccaaggtt cactaaagag caagctatgt tggtgaaggg tctttcgat   780 ttcctcggac taaattacta tattgcaaat tatgtactaa atgttcccac ttctaatagt   840
gttaatctca gctacacaac cgattctctt tctaatcaaa ctgcattccg aaatgggta   900 gctattggga gaccaactgg ggtacctgca ttttcatgt acccgaaagg attgaaagat   960
```

-continued

```
ctattggtct acacaaagga gaagtacaac gatccagtta tttacataac agagaatggc    1020
atgggtgaca acaataatgt tacaactgaa gaaggcatca aggatcccca gagggtctat    1080
ttctacaatc agcatcttct atcacttaaa aatgccattg cggctggcgt gaaggttaaa    1140
ggttacttta catgggcatt tcttgacaat tttgaatggt tatccggtta cacccaaagg    1200
ttcggaattg tctatgtaga tttcaaagat ggactaaaaa gataccccaa acattcagct    1260
ttgtggttca agaaattcct cctcaag                                        1287
```

<210> SEQ ID NO 3
<211> LENGTH: 16
<212> TYPE: PRT
<213> ORGANISM: Camellia var. sinensis
<220> FEATURE:
<221> NAME/KEY: MISC_FEATURE
<222> LOCATION: (3)..(3)
<223> OTHER INFORMATION: "Xaa" may be any amino acid

<400> SEQUENCE: 3

```
Ile Ser Xaa Gly Ser Thr Gly Asp Val Ala Asp Asp Phe Tyr His Arg
1               5                   10                  15
```

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA PCR primer

<400> SEQUENCE: 4

```
gtygcygayg ayttytayca                                                  20
```

<210> SEQ ID NO 5
<211> LENGTH: 16
<212> TYPE: DNA
<213> ORGANISM: Artificial Sequence
<220> FEATURE:
<223> OTHER INFORMATION: Synthetic DNA PCR primer

<400> SEQUENCE: 5

```
gtaaacgacg gccagt                                                      16
```

<210> SEQ ID NO 6
<211> LENGTH: 27
<212> TYPE: DNA
<213> ORGANISM: Artificial Sequence
<220> FEATURE:
<223> OTHER INFORMATION: Synthetic DNA PCR primer

<400> SEQUENCE: 6

```
ggatccatga tggcagcgaa agggtca                                          27
```

<210> SEQ ID NO 7
<211> LENGTH: 27
<212> TYPE: DNA
<213> ORGANISM: Artificial Sequence
<220> FEATURE:
<223> OTHER INFORMATION: Synthetic DNA PCR primer

<400> SEQUENCE: 7

```
gtcgacctac ttgaggagga atttctt                                          27
```

<210> SEQ ID NO 8
<211> LENGTH: 27

```
<212> TYPE: DNA
<213> ORGANISM: Artificial Sequence
<220> FEATURE:
<223> OTHER INFORMATION: Synthetic DNA PCR primer

<400> SEQUENCE: 8
ggatccgctc aaatctcctc cttcaac                                              27

<210> SEQ ID NO 9
<211> LENGTH: 27
<212> TYPE: DNA
<213> ORGANISM: Artificial Sequence
<220> FEATURE:
<223> OTHER INFORMATION: Synthetic DNA PCR primer

<400> SEQUENCE: 9
gtcgacctac ttgaggagga atttctt                                              27

<210> SEQ ID NO 10
<211> LENGTH: 27
<212> TYPE: DNA
<213> ORGANISM: Artificial Sequence
<220> FEATURE:
<223> OTHER INFORMATION: Synthetic DNA PCR primer

<400> SEQUENCE: 10
ggatccatga tggcagcgaa agggtca                                              27

<210> SEQ ID NO 11
<211> LENGTH: 27
<212> TYPE: DNA
<213> ORGANISM: Artificial Sequence
<220> FEATURE:
<223> OTHER INFORMATION: Synthetic DNA PCR primer

<400> SEQUENCE: 11
ctcgagctac ttgaggagga atttctt                                              27

<210> SEQ ID NO 12
<211> LENGTH: 27
<212> TYPE: DNA
<213> ORGANISM: Artificial Sequence
<220> FEATURE:
<223> OTHER INFORMATION: Synthetic DNA PCR primer

<400> SEQUENCE: 12
ggatccgctc aaatctcctc cttcaac                                              27

<210> SEQ ID NO 13
<211> LENGTH: 27
<212> TYPE: DNA
<213> ORGANISM: Artificial Sequence
<220> FEATURE:
<223> OTHER INFORMATION: Synthetic DNA PCR primer

<400> SEQUENCE: 13
ctcgagctac ttgaggagga atttctt                                              27

<210> SEQ ID NO 14
<211> LENGTH: 1521
<212> TYPE: DNA
<213> ORGANISM: Camellia var. sinensis
<220> FEATURE:
<221> NAME/KEY: CDS
<222> LOCATION: (1)..(1521)
<223> OTHER INFORMATION:
<221> NAME/KEY: mat_peptide
```

<222> LOCATION: (235)..()
<223> OTHER INFORMATION:

<400> SEQUENCE: 14

```
atg atg gca gcg aaa ggg tca gtt gta gtg gga gtg tta gca att gtt         48
Met Met Ala Ala Lys Gly Ser Val Val Val Gly Val Leu Ala Ile Val
        -75                 -70                 -65 gcg tat gca ctt gtt gta agt gag gtt gcc ata gca gct caa atc tcc         96
Ala Tyr Ala Leu Val Val Ser Glu Val Ala Ile Ala Ala Gln Ile Ser
    -60                 -55                 -50 tcc ttc aac aga acc agc ttt cct gat ggt ttt gtc ttt gga gct gcc        144
Ser Phe Asn Arg Thr Ser Phe Pro Asp Gly Phe Val Phe Gly Ala Ala
-45                 -40                 -35 tct tct gcc tac cag ttt gaa ggt gct gcc aag gaa ggt ggg aaa ggc        192
Ser Ser Ala Tyr Gln Phe Glu Gly Ala Ala Lys Glu Gly Gly Lys Gly
-30                 -25                 -20                 -15 ccc aat att tgg gat acc ttc act cat gag ttt cca ggt aaa ata tcg        240
Pro Asn Ile Trp Asp Thr Phe Thr His Glu Phe Pro Gly Lys Ile Ser
            -10                 -5                  -1   1 aat ggt agc act gga gat gta gct gat gac ttt tat cat cgt tac aag        288
Asn Gly Ser Thr Gly Asp Val Ala Asp Asp Phe Tyr His Arg Tyr Lys
        5                   10                  15 gaa gat gtg aag gtg ctg aag ttt ata gga cta gat ggt ttc aga atg        336
Glu Asp Val Lys Val Leu Lys Phe Ile Gly Leu Asp Gly Phe Arg Met
20                  25                  30 tcc atc tca tgg gcc cga gta tta cct cgg ggg aag ctt agc gga gga        384
Ser Ile Ser Trp Ala Arg Val Leu Pro Arg Gly Lys Leu Ser Gly Gly
35                  40                  45                  50 gtg aac aag gaa ggt atc gcc ttc tac aac aat gtc atc aat gac ctt        432
Val Asn Lys Glu Gly Ile Ala Phe Tyr Asn Asn Val Ile Asn Asp Leu
            55                  60                  65 tta tcg aaa ggt ata caa cct ttt ata aca atc ttt cac tgg gat ctt        480
Leu Ser Lys Gly Ile Gln Pro Phe Ile Thr Ile Phe His Trp Asp Leu
        70                  75                  80 ccc caa gcc cta gaa gat gaa tat gga ggc ttt tta agc cca cac att        528
Pro Gln Ala Leu Glu Asp Glu Tyr Gly Gly Phe Leu Ser Pro His Ile
    85                  90                  95 gtg aac gat ttc cgg gat ttt gca gag ctg tgc ttc aag gag ttt ggt        576
Val Asn Asp Phe Arg Asp Phe Ala Glu Leu Cys Phe Lys Glu Phe Gly
100                 105                 110 gac cga gtt aaa cat tgg atc aca atg aat gaa cca tgg tct tac tcc        624
Asp Arg Val Lys His Trp Ile Thr Met Asn Glu Pro Trp Ser Tyr Ser
115                 120                 125                 130 tat ggg gta tat gat gca ggc ctc cta gca ccg ggc cgt tgt tcg gct        672
Tyr Gly Gly Tyr Asp Ala Gly Leu Leu Ala Pro Gly Arg Cys Ser Ala
                135                 140                 145 ttt atg gca ttt tgc cct aaa ggg aat tct ggg act gag ccc tat ata        720
Phe Met Ala Phe Cys Pro Lys Gly Asn Ser Gly Thr Glu Pro Tyr Ile
            150                 155                 160 gtt acc cac aat ttg ctt ctt tct cat gct gct gct gtg aaa cta tac        768
Val Thr His Asn Leu Leu Leu Ser His Ala Ala Ala Val Lys Leu Tyr
        165                 170                 175 aag gag aaa tat cag gca tat caa aag ggg cag ata ggg ata aca cta        816
Lys Glu Lys Tyr Gln Ala Tyr Gln Lys Gly Gln Ile Gly Ile Thr Leu
    180                 185                 190 gtg act tat tgg atg att ccc tac tcc aat tcg aaa gcc gac aag gat        864
Val Thr Tyr Trp Met Ile Pro Tyr Ser Asn Ser Lys Ala Asp Lys Asp
195                 200                 205                 210 gca gca caa cga gcc ctt gat ttc atg tat gga tgg ttt att gag cca        912
Ala Ala Gln Arg Ala Leu Asp Phe Met Tyr Gly Trp Phe Ile Glu Pro
```

-continued

|  |  |  |  |  |  |  | 215 |  |  |  |  | 220 |  |  |  |  | 225 |  |  |  |
|---|---|---|---|---|---|---|---|---|---|---|---|---|---|---|---|---|---|---|---|---|
| tta | agc | ttt | ggt | gaa | tat | cca | aaa | agc | atg | cgt | aga | ctc | gtt | ggt | aaa |  |  |  |  | 960 |
| Leu | Ser | Phe | Gly | Glu | Tyr | Pro | Lys | Ser | Met | Arg | Arg | Leu | Val | Gly | Lys |  |  |  |  |  |
|  |  |  | 230 |  |  |  |  | 235 |  |  |  |  | 240 |  |  |  |  |  |  |  |

| agg | tta | cca | agg | ttc | act | aaa | gag | caa | gct | atg | ttg | gtg | aag | ggg | tct | 1008 |
| Arg | Leu | Pro | Arg | Phe | Thr | Lys | Glu | Gln | Ala | Met | Leu | Val | Lys | Gly | Ser |  |
|  |  | 245 |  |  |  |  | 250 |  |  |  |  | 255 |  |  |  |  |

| ttc | gat | ttc | ctc | gga | cta | aat | tac | tat | att | gca | aat | tat | gta | cta | aat | 1056 |
| Phe | Asp | Phe | Leu | Gly | Leu | Asn | Tyr | Tyr | Ile | Ala | Asn | Tyr | Val | Leu | Asn |  |
|  | 260 |  |  |  |  | 265 |  |  |  |  | 270 |  |  |  |  |  |

| gtt | ccc | act | tct | aat | agt | gtt | aat | ctc | agc | tac | aca | acc | gat | tct | ctt | 1104 |
| Val | Pro | Thr | Ser | Asn | Ser | Val | Asn | Leu | Ser | Tyr | Thr | Thr | Asp | Ser | Leu |  |
| 275 |  |  |  |  | 280 |  |  |  |  | 285 |  |  |  |  | 290 |  |

| tct | aat | caa | act | gca | ttc | cga | aat | ggg | gta | gct | att | ggg | aga | cca | act | 1152 |
| Ser | Asn | Gln | Thr | Ala | Phe | Arg | Asn | Gly | Val | Ala | Ile | Gly | Arg | Pro | Thr |  |
|  |  |  | 295 |  |  |  |  | 300 |  |  |  |  | 305 |  |  |  |

| ggg | gta | cct | gca | ttt | ttc | atg | tac | ccg | aaa | gga | ttg | aaa | gat | cta | ttg | 1200 |
| Gly | Val | Pro | Ala | Phe | Phe | Met | Tyr | Pro | Lys | Gly | Leu | Lys | Asp | Leu | Leu |  |
|  |  | 310 |  |  |  |  | 315 |  |  |  |  | 320 |  |  |  |  |

| gtc | tac | aca | aag | gag | aag | tac | aac | gat | cca | gtt | att | tac | ata | aca | gag | 1248 |
| Val | Tyr | Thr | Lys | Glu | Lys | Tyr | Asn | Asp | Pro | Val | Ile | Tyr | Ile | Thr | Glu |  |
|  | 325 |  |  |  |  | 330 |  |  |  |  | 335 |  |  |  |  |  |

| aat | ggc | atg | ggt | gac | aac | aat | aat | gtt | aca | act | gaa | gaa | ggc | atc | aag | 1296 |
| Asn | Gly | Met | Gly | Asp | Asn | Asn | Asn | Val | Thr | Thr | Glu | Glu | Gly | Ile | Lys |  |
| 340 |  |  |  |  | 345 |  |  |  |  | 350 |  |  |  |  |  |  |

| gat | ccc | cag | agg | gtc | tat | ttc | tac | aat | cag | cat | ctt | cta | tca | ctt | aaa | 1344 |
| Asp | Pro | Gln | Arg | Val | Tyr | Phe | Tyr | Asn | Gln | His | Leu | Leu | Ser | Leu | Lys |  |
| 355 |  |  |  |  | 360 |  |  |  |  | 365 |  |  |  |  | 370 |  |

| aat | gcc | att | gcg | gct | ggc | gtg | aag | gtt | aaa | ggt | tac | ttt | aca | tgg | gca | 1392 |
| Asn | Ala | Ile | Ala | Ala | Gly | Val | Lys | Val | Lys | Gly | Tyr | Phe | Thr | Trp | Ala |  |
|  |  |  | 375 |  |  |  |  | 380 |  |  |  |  | 385 |  |  |  |

| ttt | ctt | gac | aat | ttt | gaa | tgg | tta | tcc | ggt | tac | acc | caa | agg | ttc | gga | 1440 |
| Phe | Leu | Asp | Asn | Phe | Glu | Trp | Leu | Ser | Gly | Tyr | Thr | Gln | Arg | Phe | Gly |  |
|  |  |  | 390 |  |  |  |  | 395 |  |  |  |  | 400 |  |  |  |

| att | gtc | tat | gta | gat | ttc | aaa | gat | gga | cta | aaa | aga | tac | ccc | aaa | cat | 1488 |
| Ile | Val | Tyr | Val | Asp | Phe | Lys | Asp | Gly | Leu | Lys | Arg | Tyr | Pro | Lys | His |  |
|  |  | 405 |  |  |  |  | 410 |  |  |  |  | 415 |  |  |  |  |

| tca | gct | ttg | tgg | ttc | aag | aaa | ttc | ctc | ctc | aag |  |  |  |  |  | 1521 |
| Ser | Ala | Leu | Trp | Phe | Lys | Lys | Phe | Leu | Leu | Lys |  |  |  |  |  |  |
|  | 420 |  |  |  |  | 425 |  |  |  |  |  |  |  |  |  |  |

<210> SEQ ID NO 15
<211> LENGTH: 507
<212> TYPE: PRT
<213> ORGANISM: Camellia var. sinensis

<400> SEQUENCE: 15

Met Met Ala Ala Lys Gly Ser Val Val Gly Val Leu Ala Ile Val
            -75                 -70                 -65

Ala Tyr Ala Leu Val Val Ser Glu Val Ala Ile Ala Ala Gln Ile Ser
        -60                 -55                 -50

Ser Phe Asn Arg Thr Ser Phe Pro Asp Gly Phe Val Phe Gly Ala Ala
    -45                 -40                 -35

Ser Ser Ala Tyr Gln Phe Glu Gly Ala Ala Lys Glu Gly Gly Lys Gly
-30                 -25                 -20                 -15

Pro Asn Ile Trp Asp Thr Phe Thr His Glu Phe Pro Gly Lys Ile Ser
                -10                 -5                  -1  1

Asn Gly Ser Thr Gly Asp Val Ala Asp Asp Phe Tyr His Arg Tyr Lys
            5                   10                  15

-continued

```
Glu Asp Val Lys Val Leu Lys Phe Ile Gly Leu Asp Gly Phe Arg Met
    20                  25                  30
Ser Ile Ser Trp Ala Arg Val Leu Pro Arg Gly Lys Leu Ser Gly Gly
35                  40                  45                  50
Val Asn Lys Glu Gly Ile Ala Phe Tyr Asn Asn Val Ile Asn Asp Leu
                55                  60                  65
Leu Ser Lys Gly Ile Gln Pro Phe Ile Thr Ile Phe His Trp Asp Leu
                70                  75                  80
Pro Gln Ala Leu Glu Asp Glu Tyr Gly Gly Phe Leu Ser Pro His Ile
            85                  90                  95
Val Asn Asp Phe Arg Asp Phe Ala Glu Leu Cys Phe Lys Glu Phe Gly
        100                 105                 110
Asp Arg Val Lys His Trp Ile Thr Met Asn Glu Pro Trp Ser Tyr Ser
115                 120                 125                 130
Tyr Gly Gly Tyr Asp Ala Gly Leu Leu Ala Pro Gly Arg Cys Ser Ala
                135                 140                 145
Phe Met Ala Phe Cys Pro Lys Gly Asn Ser Gly Thr Glu Pro Tyr Ile
            150                 155                 160
Val Thr His Asn Leu Leu Leu Ser His Ala Ala Ala Val Lys Leu Tyr
        165                 170                 175
Lys Glu Lys Tyr Gln Ala Tyr Gln Lys Gly Gln Ile Gly Ile Thr Leu
    180                 185                 190
Val Thr Tyr Trp Met Ile Pro Tyr Ser Asn Ser Lys Ala Asp Lys Asp
195                 200                 205                 210
Ala Ala Gln Arg Ala Leu Asp Phe Met Tyr Gly Trp Phe Ile Glu Pro
                215                 220                 225
Leu Ser Phe Gly Glu Tyr Pro Lys Ser Met Arg Arg Leu Val Gly Lys
            230                 235                 240
Arg Leu Pro Arg Phe Thr Lys Glu Gln Ala Met Leu Val Lys Gly Ser
        245                 250                 255
Phe Asp Phe Leu Gly Leu Asn Tyr Tyr Ile Ala Asn Tyr Val Leu Asn
    260                 265                 270
Val Pro Thr Ser Asn Ser Val Asn Leu Ser Tyr Thr Thr Asp Ser Leu
275                 280                 285                 290
Ser Asn Gln Thr Ala Phe Arg Asn Gly Val Ala Ile Gly Arg Pro Thr
                295                 300                 305
Gly Val Pro Ala Phe Phe Met Tyr Pro Lys Gly Leu Lys Asp Leu Leu
            310                 315                 320
Val Tyr Thr Lys Glu Lys Tyr Asn Asp Pro Val Ile Tyr Ile Thr Glu
        325                 330                 335
Asn Gly Met Gly Asp Asn Asn Val Thr Thr Glu Glu Gly Ile Lys
    340                 345                 350
Asp Pro Gln Arg Val Tyr Phe Tyr Asn Gln His Leu Leu Ser Leu Lys
355                 360                 365                 370
Asn Ala Ile Ala Ala Gly Val Lys Val Lys Gly Tyr Phe Thr Trp Ala
                375                 380                 385
Phe Leu Asp Asn Phe Glu Trp Leu Ser Gly Tyr Thr Gln Arg Phe Gly
            390                 395                 400
Ile Val Tyr Val Asp Phe Lys Asp Gly Leu Lys Arg Tyr Pro Lys His
        405                 410                 415
Ser Ala Leu Trp Phe Lys Lys Phe Leu Lys
420                 425
```